(12) United States Patent
Masue

(10) Patent No.: US 9,561,185 B2
(45) Date of Patent: Feb. 7, 2017

(54) HYDROXYPROPYL CELLULOSE PARTICLES

(75) Inventor: Yusuke Masue, Joetsu (JP)

(73) Assignee: NIPPON SODA CO., LTD., Tokyo (JP)

( * ) Notice: Subject to any disclaimer, the term of this patent is extended or adjusted under 35 U.S.C. 154(b) by 853 days.

(21) Appl. No.: 13/393,053

(22) PCT Filed: Aug. 30, 2010

(86) PCT No.: PCT/JP2010/064690
§ 371 (c)(1),
(2), (4) Date: Feb. 28, 2012

(87) PCT Pub. No.: WO2011/027729
PCT Pub. Date: Mar. 10, 2011

(65) Prior Publication Data
US 2012/0164451 A1 Jun. 28, 2012

(30) Foreign Application Priority Data
Sep. 2, 2009 (JP) .................................. 2009-202246

(51) Int. Cl.
| | | |
|---|---|---|
| *B32B 5/16* | (2006.01) | |
| *C08B 11/02* | (2006.01) | |
| *C08B 11/08* | (2006.01) | |
| *A61K 9/16* | (2006.01) | |
| *C08B 15/02* | (2006.01) | |
| *C08L 1/28* | (2006.01) | |
| *A61K 47/38* | (2006.01) | |

(52) U.S. Cl.
CPC ............. *A61K 9/1652* (2013.01); *A61K 47/38* (2013.01); *C08B 11/02* (2013.01); *C08B 15/02* (2013.01); *C08L 1/284* (2013.01); *Y10T 428/2982* (2015.01)

(58) Field of Classification Search
CPC ...................................................... C08B 15/02
USPC ..................... 428/402; 536/88, 95
See application file for complete search history.

(56) References Cited

U.S. PATENT DOCUMENTS

| | | | | |
|---|---|---|---|---|
| 3,314,809 A | * | 4/1967 | Klug | .......................... C08B 1/08 |
| | | | | 106/179.1 |
| 3,728,331 A | * | 4/1973 | Savage | ................... C08B 11/02 |
| | | | | 536/5 |
| 6,680,069 B1 | | 1/2004 | Obara | |
| 2002/0012688 A1 | | 1/2002 | Dohi et al. | |

FOREIGN PATENT DOCUMENTS

| | | |
|---|---|---|
| CN | 1216464 A | 5/1999 |
| JP | A-05-163162 | 6/1993 |
| JP | A-06-199660 | 7/1994 |
| JP | A-09-291026 | 11/1997 |
| JP | A-10-059841 | 3/1998 |
| JP | A-10-287701 | 10/1998 |
| JP | A-2001-200001 | 7/2001 |
| JP | A-2001-322927 | 11/2001 |
| JP | A-2002-207030 | 7/2002 |
| JP | A-2005-325258 | 11/2005 |

OTHER PUBLICATIONS

Machine translation of JP 2002-207030 (2002).*
Excipients NISSO HPC Application Note, Note # CR-2012-AAPS (2012).*
Oct. 12, 2010 International Search Report issued in International Patent Application No. PCT/JP2010/064690 (with translation).
Handbook of Pharmaceutical Excipients, revised edition, Yakuji Nippo Ltd., Feb. 28, 2007, pp. 700-705.
Mitsuru Hashida, Keiko Toyo Seizai no Sekkei to Hyoka, Kabushiki Kaisha Yakuji Jihosha, Feb. 10, 1995, pp. 168-171.
Oct. 12, 2010 Written Opinion of the International Searching Authority issued in International Patent Application No. PCT/JP2010/064690 (with Translation).
Apr. 3, 2013 Office Action issued in Chinese Application No. 201080038106.0 (with translation).
May 29, 2014 Decision for Grant of Patent issued in Korean Application No. 2012-7005257 with English-language translation.
Mar. 18, 2014 European Office Action issued in European Application No. 10 813 678.9.

* cited by examiner

*Primary Examiner* — Holly Le
(74) *Attorney, Agent, or Firm* — Oliff PLC

(57) ABSTRACT

Hydroxypropyl cellulose particles which contain 50-100 weight % of particles with a particle size that is larger than 150 μm and not larger than 355 μm.

2 Claims, No Drawings

HYDROXYPROPYL CELLULOSE PARTICLES

TECHNICAL FIELD

The present invention relates to hydroxypropyl cellulose particles. More specifically, the present invention relates to hydroxypropyl cellulose particles which are dissolved in water or organic solvent for use.

Priority is claimed on Japanese Patent Application No. 2009-202246, filed Sep. 2, 2009, the content of which is incorporated herein by reference.

BACKGROUND ART

Hydroxypropyl cellulose is a hydroxy ether which is obtained by reacting propylene oxide with cellulose. Hydroxypropyl cellulose is used as a binder or forming base material which is added to solid pharmaceutical preparations such as granules and tablets, as a binder for manufacturing ceramics, as a film or coating agent, or as a food additive, thickener, stabilizer, gelator, paste agent, emulsifier, dispersant, adhesive, and so on.

Hydroxypropyl cellulose is ordinarily supplied in particle form. As particulate hydroxypropyl cellulose, for example, Patent Document 1 discloses hydroxypropyl cellulose particles with a particle size of 1-150 µm for use in the adhesive layer of an adhesive patch. In addition, Patent Document 2 and Patent Document 3 record low substituted hydroxypropyl cellulose particles with a volume average particle size of 25 µm or less, measured by a dry laser diffraction method, for use in solid preparations.

PRIOR ART REFERENCES

Patent Documents

Patent Document 1: Japanese Unexamined Patent Application, First Publication No. H06-199660
Patent Document 2: Japanese Unexamined Patent Application, First Publication No. 2001-200001
Patent Document 3: Japanese Unexamined Patent Application, First Publication No. 2001-322927
Patent Document 4: Japanese Unexamined Patent Application, First Publication No. 2002-207030

DISCLOSURE OF INVENTION

Problems to be Solved by the Invention

When the hydroxypropyl cellulose particles of small particle size disclosed in these patent documents are infused into water, unresolved particles frequently occur in a clumped state.

The object of the present invention is to offer hydroxypropyl cellulose particles which rapidly dissolve in water without clumping, and which inhibit occurrence of unresolved particles.

Means for Solving the Problems

As a result of diligent study aimed at solving the aforementioned problem, the present inventor discovered that solubility in water is enhanced when hydroxypropyl cellulose particles of specific particle distributions are used. The present invention was perfected by further study based on this finding.

That is, the present invention includes the following modes.

(1) Hydroxypropyl cellulose particles which contain 50-100 weight % of particles with a particle size that is larger than 150 µm and not larger than 355 µm.

(2) The hydroxypropyl cellulose particles recorded in (1), wherein the aforementioned hydroxypropyl cellulose particles contain 100 weight % of particles with a particle size that is larger than 150 µm and not larger than 355 µm (3) Hydroxypropyl cellulose particles which contain 50-100 weight % of particles with a particle size that is larger than 250 µm and not larger than 355 µm.

(4) The hydroxypropyl cellulose particles recorded in (3), wherein the aforementioned hydroxypropyl cellulose particles contain 100 weight % of particles with a particle size that is larger than 250 µm and not larger than 355 µm.

(5) Hydroxypropyl cellulose particles which contain 50-100 weight % of particles with a particle size that is larger than 180 µm and not larger than 250 µm.

(6) The hydroxypropyl cellulose particles recorded in (5), wherein the aforementioned hydroxypropyl cellulose particles contain 100 weight % of particles with a particle size that is larger than 180 µm and not larger than 250 µm.

(7) The hydroxypropyl cellulose particles recorded in any one of (1), (3) and (5), wherein the content of hydroxypropyl groups is 53.4-77.5 weight %, and viscosity at 20° C. in a 2% aqueous solution is in a range of 100-5000 mPa·s.

Effects of the Invention

When the hydroxypropyl cellulose particles of the present invention are infused into water, they rapidly dissolve in water without clumping, and inhibit occurrence of unresolved particles.

By dissolving the hydroxypropyl cellulose particles of the present invention in water or organic solvent, it is possible to promote viscosity control, gelation, and stabilization of the solution.

BEST MODE FOR CARRYING OUT THE INVENTION

With respect to the hydroxypropyl cellulose particles of the present invention, particles with a particle size that is larger than 150 µm and not larger than 355 µm are 50-100 weight %, preferably 80-100 weight %, and more preferably 100 weight % of total particles.

With respect to the preferred hydroxypropyl cellulose particles of the present invention, particles with a particle size that is larger than 250 µm and not larger than 355 µm are 50-100 weight %, preferably 70-100 weight %, and more preferably 100 weight % of total particles.

Furthermore, with respect to the hydroxypropyl cellulose particles of the present invention, it is preferable that particles with a particle size that is not larger than 150 µm be 20 weight % or less of total particles. In addition, with respect to the hydroxypropyl cellulose particles of the present invention, it is preferable that particles with a particle size that is not larger than 250 µm be 30 weight % or less of total particles.

When hydroxypropyl cellulose particles having such particle size distributions are infused into water, they rapidly dissolve in water without clumping, and inhibit occurrence of unresolved particles.

Particle size distribution in the present invention is classified using a 150 µm sieve, 180 µm sieve, 250 µm sieve, 355

μm sieve, and 500 μm sieve, and is calculated from the respective quantities above the sieve and below the sieve.

Hydroxypropyl cellulose is obtained, for example, by producing alkali cellulose from the action of sodium hydroxide on cellulose raw material, and by subsequently causing a substitution reaction of alkali cellulose and propylene oxide. As a result of this substitution reaction, a portion or the entirety of the —OH groups in the glucose ring unit of cellulose is replaced by —O—(CH2CH(CH3)O)m-H groups. Here, m is a natural number of 1 or more. After the substitution reaction, the sodium hydroxide is neutralized by adding acid such as acetic acid or hydrochloric acid to the reaction liquid, and the hydroxypropyl cellulose particles can then be obtained by purification, granulation, and classification. There are no particular limitations on the granulation method. For example, one may cite methods such as pulverization, spray drying, and crystallization.

The bulk powder obtained in the foregoing manner is classified to obtain the aforementioned particle size distribution. As for the classification method, one may cite, for example, methods such as sieving, centrifugal classification, and gravitational classification—of these, sieving is preferable.

With respect to the hydroxypropyl cellulose particles of the present invention, the content of hydroxypropyl groups (—(CH2CH(CH3)O)m-H) is preferably in a range of 53.4-77.5 weight %, and more preferably in a range of 62-77.5 weight %. When the content of hydroxypropyl groups is within this range, obtainment of hydroxypropyl cellulose particles with little insolubility in water is facilitated. The content of hydroxypropyl groups may be obtained by the method of USP24 United States Pharmacopeia), or by the method recorded in Patent Document 4.

With respect to the hydroxypropyl cellulose particles of the present invention, viscosity at 20° C. in 2% aqueous solution is preferably in a range of 100-5000 mPa·s, and more preferably in a range of 150-4000 mPa·s. Viscosity is an indicator which expresses the degree of polymerization of the hydroxypropyl cellulose. When viscosity is within the aforementioned range, it is possible to easily obtain the desired physical properties with additions in small amounts.

The hydroxypropyl cellulose particles of the present invention may be used as a binder or forming base material which is added to solid preparations such as granules and tablets, as a binder for purposes of manufacturing ceramics, as a film or coating agent, or otherwise as a viscosity control agent, dispersant, adhesive, and so on. Among these, the hydroxypropyl cellulose particles of the present invention are well-suited to a mode of use by dissolution in water or organic solvent. For example, they may be preferably used as food additives, thickeners, stabilizers, gelators, pastes, emulsifiers, dispersants, adhesives, and the like.

EXAMPLES

Next, working examples are presented to describe the present invention in greater detail. The present invention is not limited by these working examples.

Working Example 1

A sample was obtained by thoroughly mixing 2 g of hydroxypropyl cellulose particles (CELNY-M, manufactured by Nippon Soda Co., Ltd.) and 2 g of dextrose. The hydroxypropyl cellulose particles contain 42 weight % of particles larger than 150 μm and not larger than 350 μm. 396 g of distilled water were poured at room temperature into a 500 ml tall beaker, and left standing. The sample was added to this. After addition, stirring was conducted for approximately 10 seconds at 4 on the stirring intensity scale using an octagonal rotator with a magnetic stirrer (model AMG-H, manufactured by ASH Co.). Subsequently, stirring was lowered to 2 on the stirring intensity scale, and conducted for 15 seconds. The state of dissolution of the sample in the beaker was visually observed. As a result, it was observed that clumping had formed on the surface, and that unresolved particles existed on the bottom, but it was within a scope that permitted use.

Working Examples 2-4, Comparative Examples 1-3

Preparation of Hydroxypropyl Cellulose Particles

Hydroxypropyl cellulose particles were prepared in the following manner. A sheet of hydroxypropyl cellulose (viscosity at 20° C. in 2% aqueous solution: 352-414 mPa·s) was pulverized in a cutter mill to obtain bulk powder. This was classified with a 150 μm sieve, 180 μm sieve, 250 μm sieve, 355 μm sieve, and 500 μm sieve to respectively obtain particles with a particle size that is larger than 355 μm and not larger than 500 μm, particles with a particle size that is larger than 150 μm and not larger than 180 μm, particles with a particle size that is larger than 180 μm and not larger than 250 μm, particles with a particle size that is larger than 250 μm and not larger than 355 μm, particles with a particle size that is larger than 150 μm and not larger than 355 μm, and particles with a particle size that is not larger than 150 μm. Solubility testing (working examples 2-4, comparative examples 1-3) was conducted by the same method as working example 1, and the results are shown in Table 1.

TABLE 1

| | Particle size range (μm) | State of dissolution | | |
| --- | --- | --- | --- | --- |
| | | Immediately after addition | At start of stirring | After 15 minutes of stirring |
| Working example 2 | Larger than 150 μm and not larger than 355 μm | Do not precipitate even when permeated, and float on the surface. | There are small clumps which disperse after a while. | Mostly dissolve, but there is a minute amount of unresolved particles. |
| Working example 3 | Larger than 250 μm and not larger than 355 μm | Immediately undergo permeation, and precipitate. | Dispersion is satisfactory, without clumping. | Mostly dissolve, but there is a minute amount of unresolved particles. |

TABLE 1-continued

|  | Particle size range (μm) | State of dissolution | | |
|---|---|---|---|---|
|  |  | Immediately after addition | At start of stirring | After 15 minutes of stirring |
| Working example 4 | Larger than 180 μm and not larger than 250 μm | Are permeated, and precipitate. | Dispersion is satisfactory, without clumping. | Mostly dissolve, but there is a small amount of unresolved particles. |
| Comparative example 1 | Larger than 150 μM and not larger than 180 μm | Do not precipitate. | Dispersion is satisfactory, without clumping. | There are unresolved particles on the order of 1 cm on the surface. |
| Comparative example 2 | Not larger than 150 μm | Dispersion is poor. | Small clumps form. Undispersed particles exist at the central region of stirring. | Large clumps of more than 2 cm form on the surface. There are no unresolved particles at the bottom. |
| Comparative example 3 | Larger than 355 μm and not larger than 500 μm | Are permeated, and precipitate. | There is dispersion without clumping. | There are many unresolved particles. |

INDUSTRIAL APPLICABILITY

When the hydroxypropyl cellulose particles of the present invention are infused into water, they dissolve rapidly in water without clumping, and inhibit unresolved particles. Consequently, the hydroxypropyl cellulose particles of the present invention can be dissolved in water or organic solvent to achieve viscosity control, gelation, and stabilization of the solution, exhibiting industrial usefulness.

The invention claimed is:

1. Hydroxypropyl cellulose particles which contain 100 weight % of particles with a particle size that is larger than 250 μm and not larger than 355 μm, wherein a content of hydroxypropyl groups is 53.4 to 77.5 weight %, and viscosity at 20° C. in a 2% aqueous solution is in a range of 100 to 5000 mPa·s.

2. Hydroxypropyl cellulose particles which contain 100 weight % of particles with a particle size that is larger than 180 μm and not larger than 250 μm, wherein a content of hydroxypropyl groups is 53.4 to 77.5 weight %, and viscosity at 20° C. in a 2% aqueous solution is in a range of 100 to 5000 mPa·s.

* * * * *